United States Patent [19]
Shuler et al.

[11] Patent Number: 5,656,610
[45] Date of Patent: Aug. 12, 1997

[54] PRODUCING A PROTEIN IN A MAMMAL BY INJECTION OF A DNA-SEQUENCE INTO THE TONGUE

[75] Inventors: Charles P. Shuler, Westlake Village; Lawrence H. Kedes; Theodore I. Prigozy, both of Los Angeles, all of Calif.

[73] Assignee: University of Southern California, Los Angeles, Calif.

[21] Appl. No.: 263,108

[22] Filed: Jun. 21, 1994

[51] Int. Cl.$^6$ .............................. A61K 48/00; C12N 15/00
[52] U.S. Cl. ............................. 514/44; 935/53; 935/56; 935/63
[58] Field of Search .................... 514/44; 424/93.2

[56] References Cited

PUBLICATIONS

Acsadi et al (1991) Nature 352, 815–818.
Prigozy et al (1993) Somat. Cell Molec. Gen. 19, 111–122.

Primary Examiner—Jasemine C. Chambers
Assistant Examiner—Deborah Crouch
Attorney, Agent, or Firm—Robbins, Berliner & Carson

[57] ABSTRACT

The striated muscle of the tongue of an animal (in particular, a mammal) is employed as the target tissue for direct DNA injection of an exogenous polynucleotide sequence encoding a biologically active molecule. The DNA is incorporated into the tongue muscle cells and the polypeptide encoded thereby expressed, resulting in the production of a biologically active molecule. Superior levels of expression of the injected exogenous polynucleotide are achieved relative to injection in other types of cells, in particular other types of muscle cells. Moreover, the striated muscle of the tongue represent an easily accessed anatomic location that has not previously been used for direct DNA injection.

9 Claims, 5 Drawing Sheets

FIG. 1
a) pβ-actin CAT
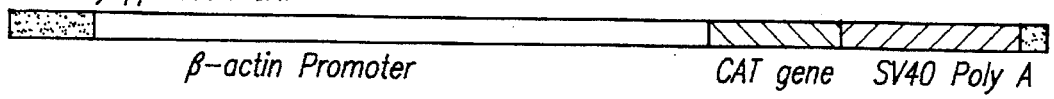
β-actin Promoter   CAT gene   SV40 Poly A
b) pMaori3
CMV ie1   nLacZ   Poly A Ori
c) pM3-TnC3
U P   nLacZ   Poly A Ori
d) pTnC-F CAT
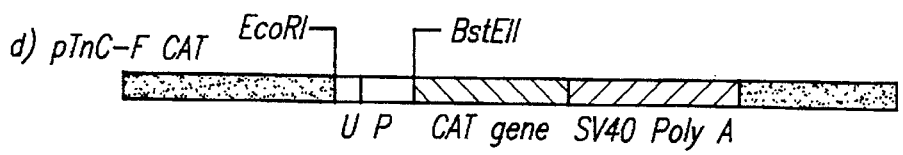
U P   CAT gene   SV40 Poly A
e) pSV40/TnC-F CAT
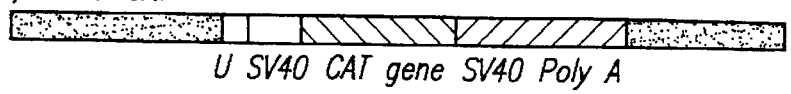
U SV40 CAT gene   SV40 Poly A
f) pSV40 CAT
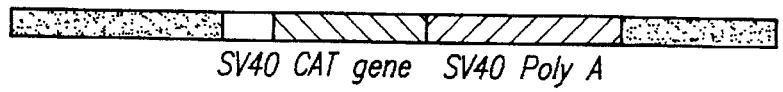
SV40 CAT gene   SV40 Poly A
g) pRSV-luciferase
RSV LTR   Luciferase gene   SV40 Poly A
—— 500 bp

PRODUCING A PROTEIN IN A MAMMAL BY INJECTION OF A DNA-SEQUENCE INTO THE TONGUE

BACKGROUND OF THE INVENTION

The present invention relates generally to the fields of biochemistry and medicine. In particular, the present invention relates to methods for use in delivering one or more exogenous polynucleotide sequences to muscle cells of an animal, in particular a mammal, so as to achieve an enhanced therapeutic effect thereon.

Various approaches have been suggested for the introduction of exogenous polynucleotide sequences into human or animal patients (generally referred to as "gene therapy"). Various techniques for integration of exogenous DNA into the genome of a cell have been proposed. Unfortunately, such integration can cause damage to the genome and possible genetic changes in the recipient cell which might predispose the cells to malignancy. Therefore, methods which avoid these potential problems would be desirable in providing safe and effective techniques of gene therapy.

The introduction of plasmid DNA into striated muscles by direct injection has been described in limb, trunk, and heart [Wolff, J. A. et at. (1990) Science 247:1465–1468; Lin, H. et al. (1990) Circulation 82:2217–2221; Acid, G. et at. (1991) New Biol. 3:71–81; Kitsis, R. et al. (1991) Proc. Natl. Acad. Sci. U.S.A. 88:4138–4142]. In addition, PCT published application WO 90/11092 (the entire disclosure of which is hereby incorporated by reference) generally describes the delivery of a purified polynucleotide to the interior of a cell or cells of a vertebrate, wherein the delivered material consists of a pharmaceutically acceptable carrier and a naked polynucleotide which encodes either a polypeptide or an antisense polynucleotide. Although a variety of types of cells (including, in particular, muscle cells) are suggested as target cells, there is no specific disclosure of the injection of polynucleotide into the tongue. WO 90/11092 proposes that the polynucleotide is integrated into the genomic DNA of the cell or cells and subsequently produces a messenger RNA which serves to encode a polypeptide with either pharmaceutical or immunogenic properties. The polypeptide may be released into the interstitial spaces surrounding the cell or function inside the cell. Alternatively, the integrated polynucleotide encodes a RNA sequence which inhibits in a cell the production of a polypeptide which is associated with a detrimental effect on either the cell or the entire organism. The methods described in WO 90/11092 are alleged to result in either immunogenic or pharmacological effects on the vertebrate through several means, including delivering a therapeutic polypeptide to the cells of the vertebrate and providing a transitory method of gene therapy. Although the direct injection of DNA is a relatively simple methodology, the levels of expression achieved to date have not at all been satisfactory for reliable achievement of therapeutic or other physiological effects on mammals so treated.

It is an object of the present invention to provide methods and compositions for achieving enhanced levels of expression of exogenous polynucleotide in animals upon direct injection of the polynucleotide into the mammal.

SUMMARY OF THE INVENTION

Pursuant to the present invention, the striated muscle of the tongue of an animal (and in particular, of a mammal) is employed as the target tissue for direct DNA injection. The DNA is incorporated into the tongue muscle cells and the polypeptide encoded thereby expressed, resulting in the production of a biologically active molecule. Superior levels of expression of the injected exogenous polynucleotide are achieved relative to injection in other types of cells, in particular other types of muscle cells. Moreover, the striated muscle of the tongue represent an easily accessed anatomic location that has not previously been used for direct DNA injection.

BRIEF DESCRIPTION OF THE DRAWINGS

The invention may be better understood with reference to the accompanying drawings, in which:

FIG. 1 depicts the construction of expression plasmids employed in accordance with the present invention;

DETAILED DESCRIPTION OF THE INVENTION

Figure 2:
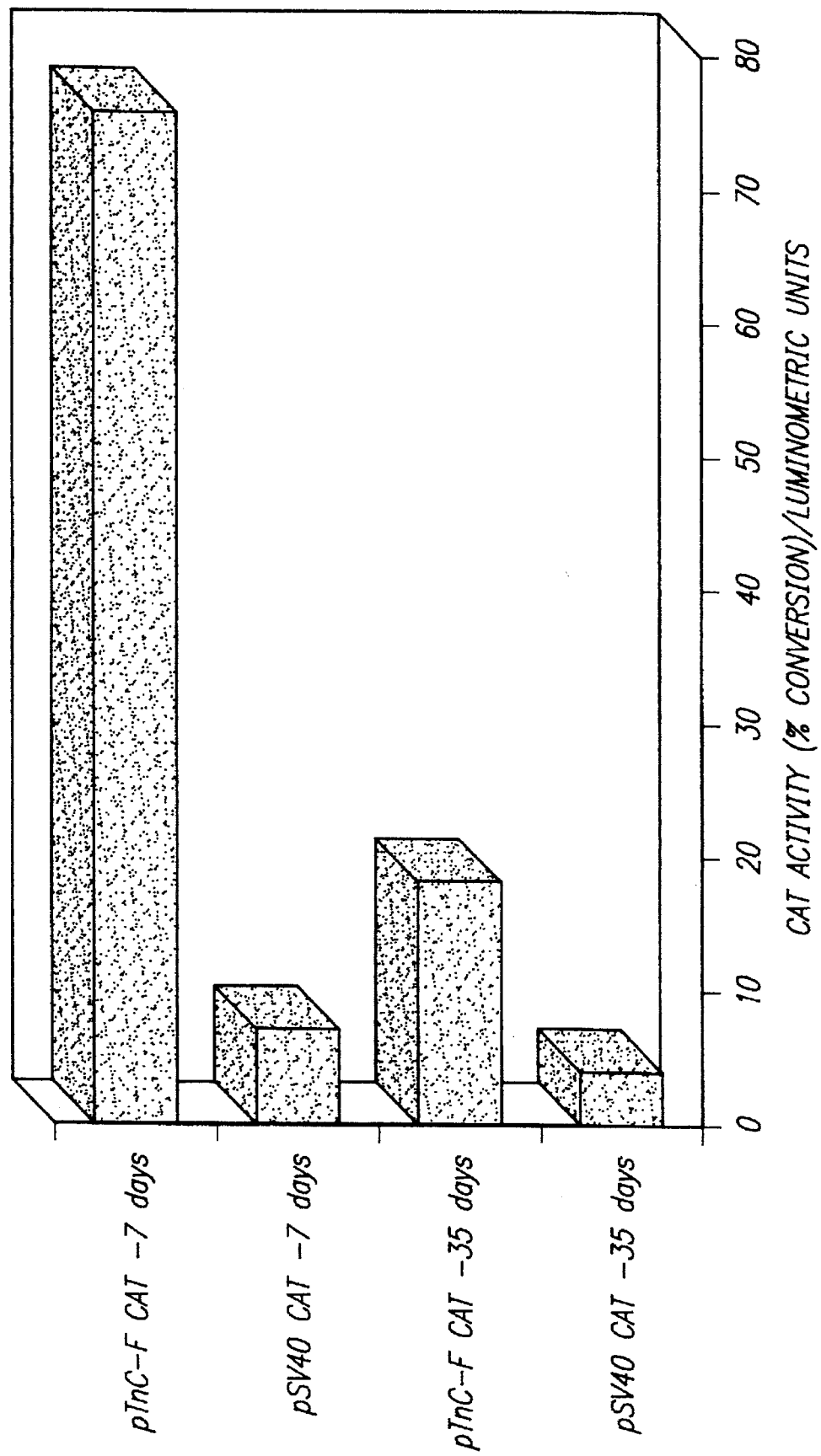
FIG. 2 illustrates the levels of CAT activity after injection with various expression vectors in accordance with the present invention.

The tongue is defined as the movable muscular organ on the floor of the mouth in many animals, including in particular mammals. It subserves the special sense of taste, aiding in mastication, deglutition and the articulation of sound. The tongue consists of a few defined intrinsic muscle groups that include the Genioglossus, the Longitudinalis Superior, the Longitudinalis Inferior, and the Transversus. These muscle groups are defined primarily by their direction of orientation, and all are required for tongue function. The muscles are also intertwined and not separately isolated. The tongue muscles are supported by a rich vascular network associated with a high rate of blood flow. The tongue muscles are covered only by a very small layer of connective tissue and a characteristic stratified squamous epithelium. Percutaneous injection into the tongue muscle is facilitated by the lack of the well-defined fascial membrane surrounding other striated muscles. Injection into any or all of these muscles groups is contemplated as within the scope of the present invention.

In some instances, a single injection of the polynucleotide construct may be sufficient; in others, multiple injections may be appropriate. Therefore, the present invention contemplates both single-injection and multiple-injection protocols to deliver the polynucleotide into the tongue muscle. The preferred course of injection for any given construct may be readily determined empirically.

The striated muscle of the tongue presents several advantages for use in direct DNA injection studies. The ease of accessibility of the tongue can expedite the injection of large numbers of animals and the dense musculature enables large amounts of material to be introduced by direct injection. The tongue is also easily accessible at very young ages, thus permitting introduction of desired molecules (e.g., growth factors or growth hormones) at early stages of growth and providing a muscle model suitable for developmental characterization of gene regulation.

In accordance with the present invention, it has been determined that expression of exogenous genes in the striated tongue muscle occurs at high levels relative to that observed in different muscles or other types of cells. Given the general understanding of those working in the field (for example, as exemplified by PCT application WO 90/11092) that all types of muscle cells would be roughly equivalent for this purpose, it is surprising that substantially higher levels of expression are achieved in accordance with the present invention by injection into tongue muscle only.

Pursuant to the method of the present invention, the injected DNA typically comprises a naked polynucleotide construct including at least one gene encoding a biologically-active polypeptide of interest operatively linked to a promoter sequence, which drives expression of the gene. Plasmid expression vectors may be used that contain either constitutive or muscle-specific promoters directing the transcription of genes. Presently preferred are promoter sequences which are specific for muscle cells. In addition to the promoters described in the examples herein, other promoter sequences of utility in the constructs employed in the present invention include, but are not limited to, the following: tetracycline inducible promoter [Faryar, K. & Gatz, C. (1992) *Current Genetics* 21:345–349; Gossen, M. & Bujard, H. (1992) *Proc. Natl. Acad. Sci. USA* 89:5547–5551]; zinc inducible metallothionein promoter [McNeall, J. et al. (1989) *Gene* 76:81–88; Hu, M. & Davidson, N. (1990) *Mol. Cell. Biol.* 10:6141–6151]; inducible stress protein promoters [Lee, A. S. (1992) *Current Opinion in Cellular Biol.* 4: 267; Liu, E. S. & Lee, A. S. (1992) *Nucleic Acids Research* 19:5425]; muscle creating kinase promoter [Bishopric, N. H. et al. (1991) "Gene expression during skeletal and cardiac muscle development," in *The Heart and Cardiovascular System*, Raven Press]; myosin heavy chain promoter [Wade, R. & Kedes, L (1989) "Developmental regulation of contractile protein genes," in *Annual Reviews of Physiology*, Annual Reviews Inc., pp. 179–188]. The sequences for these and other suitable promoters have been reported in the literature, and the isolation or synthesis thereof would be well within the skill of those working in the field. Suitably, the gene for the polypeptide of interest also includes the necessary sequence(s) to direct secretion or transport of the gene product out of the cells and into the circulation.

The naked polynucleotide constructs used according to the method of the present invention comprise DNA sequences coding for polypeptides which have useful therapeutic applications (i.e., are biologically active). These polynucleotide constructs are naked in the sense that they are free from any delivery vehicle, which would act to facilitate entry into the cell (e.g., viral sequences) and/or to promote transfection (e.g., liposomes, polybrene, divalent cations). Preferably, the sequences used in the method of the invention do not integrate into the genome of the host cell, but rather remain in the cell as episomal elements.

The polynucleotides generally code for physiologically active or therapeutic polypeptides. For purposes of the present invention, a polypeptide is understood to be the translation product of a polynucleotide, regardless of size and glycosylation. Physiologically active polypeptides are those that have an effect on the growth or metabolism of the organism being treated. Therapeutic polypeptides include those that compensate for defective or deficient species in the target animal or those that act through toxic effects to limit or remove harmful cells from the body. One class of polypeptides of particular interest in accordance with the present invention are growth factors and growth hormones. Other polypeptides of interest include, but are not limited to, the following: insulin, erythropoietin, tissue inhibitor of metalloproteinase (TIMP), tumor necrosis factor, interleukins, interferons, tissue plasminogen activator, factor VIII, proteins which stimulate the growth of fur and hair, immunogenic polypeptides, immunomodulatory peptides, etc. Sequences for these polypeptides (or functional equivalents thereof) are known or may be determined using essentially routine techniques.

The polynucleotide is generally a DNA sequence which either is self-replicating, or is itself non-replicating but is inserted into a plasmid or other vector which further comprises a replicator. Presently preferred are plasmid constructs which may be propagated in high copy number in suitable bacteria or other hosts (e.g., yeast, cell cultures, etc.). Particular vectors for use in preparing DNA constructs for purposes of the present invention include, but are not limited to, the following: pBR322, pSV40, pUC19, pGEM, pSP70, pSP71, pGL2, pEUK, pMAM, pSE280, pCDM8, pSPORT1, pSK and pOPRSVI. Suitable plasmids and methods for constructing same so as to include genes encoding for physiologically active polypeptides have been extensively reported in the literature and scores of plasmids are commercially available. It would be immediately apparent to those working in the field which of these plasmids would be suitable for use in accordance with the present invention. Moreover, manipulation of these plasmids to insert suitable promoter sequences and genes coding for polypeptides of interest in the proper reading frame would be well within the level of skill of those currently working in the field. The construction of a number of suitable vectors for use in the present invention is illustrated in the examples herein.

The DNA construct may suitably also comprise recognition sites for cellular polymerases so as to facilitate transcription. Further, the DNA construct preferably comprises a replicator (e.g., replicator pMB1 for plasmid pBR322).

Given the current state of the art, all or portions of the DNA constructs for use in the present invention can be synthesized directly when the nucleotide sequence is known. Alternatively, various PCR and cloning techniques may be employed to provide the desired sequences for preparation of the DNA constructs employed in accordance with the present invention.

In general, an effective dose of the DNA construct will be in the range of about 0.01 µg/kg to about 100 mg/kg, and preferably about 0.001 mg/kg to about 10 mg/kg. The appropriate dosage for any given construct may be readily determined empirically and will depend upon a number of factors, including the activity of the peptide encoded by the construct. The DNA constructs may be suitably administered in the form of pharmaceutically-acceptable salts, as generally known in the art. As suitable vehicle for administration of the DNA constructs, any of a wide range of known liquid vehicles may be employed. The DNA constructs may be formulated as emulsions, suspensions or solutions in oily or preferably aqueous vehicles. The compositions may further comprise customary additives, such as buffers to provide a suitable pH and nonionic materials (e.g., glucose) for adjusting tonicity. The compositions per unit dosage suitably comprise from about 0.1% to about 99% of the DNA construct.

In experiments carried out in accordance with the present invention, the expression of the injected plasmids was directly correlated with the mass of injected DNA and the time of incubation following the injection. Simultaneous injection of two individual expression vectors bearing either chloramphenicol acetyl transferase (CAT) or luciferase reporter genes resulted in a dose-dependent level of expression for each of the plasmids. The linearity of the coexpression thus provided a means to normalize DNA uptake and analyze promoter efficiency.

The dose- and time-response analyses of CAT, luciferase and β-galactosidase activity, following direct injection of plasmids expressing these reporter genes, showed that the tongue muscle was properly responsive to the amount of DNA initially injected and the subsequent length of incubation. In every case, the reporter gene was expressed soon after injection and reached a maximal level of expression at one week after injection. The dose-related gene activity was also reproducible and provided results that had a distinct and broad linear range that allowed the use of coinjected plasmids to normalize DNA uptake and permit functional analyses of promoter elements.

The invention may be better understood with reference to the accompanying examples, which are intended for purposes of illustration only and should not be construed as in any sense limiting the scope of the present invention, as defined in the claims appended hereto.

EXAMPLES

In the following examples, all chemicals used were of the highest reagent grade available. Acetyl-CoA, luciferin, ATP, and glycylglycine were purchased from Sigma Chemical Co. Carbon-14-labeled chloramphenicol was purchased from Amersham. 5-Bromo-4-chloro-3-indolyl-B-D-galactopyranoside (X-gal) was obtained from Boehringer Mannheim Biochemicals. Restriction endonucleases and DNA-modifying enzymes were purchased from either Promega Biotech or Boehringer Mannheim.

EXAMPLE 1

Several expression plasmids were used in this example. The sequence and specific domains of each plasmid are depicted in FIG. 1. The pβ-actin CAT is a PBR322-derived plasmid. pMaori3 is a pUC19-derived plasmid; the reporter gene nLacZ consists of the *E. coli* LacZ gene fused 3' of a 30-bp sequence that encodes the 10 amino acid nuclear localization signal of the SV40 large T antigen and the poly A addition sequences from the mouse protamine 1 gene. The pTnC-F CAT plasmid was constructed by deletions of internal sequences in the TnC-F promoter and ligation such that the URE (−1625 to −1500) is linked to the proximal promoter (−193 to +56) and these two elements promote expression of the CAT gene [see, e.g., Gahlman, R. & Kedes, L. (1990) *J. Biol. Chem.* 265:12520–12528; Gahlman, R. & Kedes, L. (1993) *Gene Expression* 3:11–25]; the positions of the EcoRI and BstEII sites are indicated to illustrate the construction of pM3–TnC3. The pM3–TnC3 plasmid was constructed by replacing the CMV promoter of the plasmid pMaori3 with the human TnC-F gene regulatory elements previously described. pM3–TnC3 is a pMaori3 derivative in which the CMV promoter [Boshart, M. et al. (1985) Cell 41:521–530] has been replaced with the EcoRI-BstEII restriction fragment containing the upstream enhancer (U) and the proximal promoter (P) of the human troponin C-fast gene. Both pMaori3 and pM3–TnC3 have the SV40 large T antigen nuclear localization signal sequence. The pRSV-luciferase plasmid is a pBR322 derivative.

The pSV40 CAT plasmid was obtained from Promega and the TnC-F URE (−1625 to −1500) was cloned into the BglII site of this vector in the sense orientation. The preparation of the pg-actin CAT plasmid has been previously described [Gunning, P. et at. (1987) *Proc. Natl. Acad. Sci. USA* 84:4831–4835], as has the pRSV-luciferase [de Wet, J. R. et al. (1987) *Mol. Cell Biol.* 7:725–737].

All plasmids were purified by two cesium chloride gradients and extensively dialyzed against 10 mM EDTA. The purified plasmid DNA was ethanol precipitated and dissolved in 0.9% sodium chloride [Wolff, J. A. et at., (1991) Biotechniques 11:474–485]. The quality and integrity of the DNA was assessed by absorbance readings at 260 and 280 nm and by agarose electrophoresis.

Adult Swiss-Webster and B10 mice were anesthetized with 3 mg of ketamine and 0.5 mg of xylazine by intraperitoneal injection. The tongues were pulled out of the mouth slightly with a forceps to allow a 30-gauge needle to penetrate the bulk of the tongue muscle. A 100-μl volume of DNA was delivered at a speed of approximately 20 μl/sec. Animals were always injected with a 100 μl volume of DNA-normal saline solution, but the concentration of DNA differed based upon the experimental protocol as hereinafter described. After the injection, the tongues immediately swelled due to the injected fluid but the tongues returned to the normal volume within a short period of time. The tongue injection did not impair the ability of the animals to either eat or drink following recovery from anesthesia, and there were no fatalities from this injection procedure.

At specific time points following the direct injection of the DNA the animals were euthanized and the tongues removed. Samples were processed for both luciferase and CAT activities by the following method. The individual tongues were homogenized in 25 mM $MgSO_4$, 4 mM EGTA, 1 mM DTT, and 0.1% Triton X-100 (500 μl) using a Tissue Tearor (Whatman). The homogenates were then centrifuged for 15 minutes (9500 g, 4° C.). Aliquots of either 50, 75 or 100 μl of the resulting supernatant were used directly for the luciferase assay. The same homogenates were used for CAT assay; however, prior to the CAT assay the homogenates were heated at 65° C. for 10 minutes to inactivate any endogenous deacetylase enzymes. The protein concentrations of the homogenates were determined by the Bradford method.

For the luciferase assay, an aliquot of the tongue muscle homogenate was added to 350 μl of a 2.5 mM ATP solution containing 15 mM potassium phosphate in addition to the components of the homogenization solution. The reaction was mixed in the reaction chamber of a Monolight 2001 luminometer and the reaction started by injection of 100 μl of 0.125 mM d-luciferin. Luminometric output was measured at a peak setting of 10 seconds. The luminometric units were standardized to the amount of protein used in the assay.

For the CAT assay, the homogenate was mixed with 50 μl of 25 mM acetyl-CoA 5 μl of [$^{14}$C]chloramphenicol, and adjusted to a total volume of 200 μl. The mixture was incubated at 37° C. for 14 hours. The reaction mixtures were then extracted with ethyl acetate and dried in a Speed-Vat concentrator (Savant Instruments). The dried products were dissolved in 25 μl of ethyl acetate prior to loading on Baker-flex silica gel thin-layer chromatography (TLC) plates. The reaction products were separated with chloroform-methanol (95:5) as the mobile phase for the TLC. The TLC plates were scanned with an AMBIS radioanalytic scanner to quantitate the percentage of CAT conversion.

For staining of nuclear localized β-galactosidase, tongues injected with either pMaori3 or pM3–TnC3 were removed, frozen on dry ice, and serially thick sectioned. The sections were fixed in 4% paraformaldehyde for 30 minutes. The fixed sections were incubated with 1 mM X-gal, 5 mM potassium ferricyanide, 5 mM potassium ferrocyanide, and 2 mM magnesium chloride in 0.1 M PBS, pH 7.3, for 1 hour at 37° C. [Sanes, J. R. et al. (1986) EMBO J. 5:3133–3142]. The pattern of nuclear β-galactosidase localization staining was examined by light microscopy using an EDGE high-resolution stereoscopic microscope and recorded photographically on Kodak T-Max 400 film.

To determine the DNA dose and incubation time necessary to assay CAT activity, the tongue muscles of mice were injected with either 10, 20 or 50 µg of pβ-actin-CAT DNA in 100 µl normal saline. The animals were killed and the tissue removed either four or seven days after the injection. The CAT activity was determined in each of the injected tongue muscles at both incubation times. The highest level of CAT activity was present in tongue muscles injected with 50 µg of plasmid and analyzed seven days later. CAT activity was present and readily quantified in all the tongue muscles injected with either smaller amounts of pβ-actin-CAT plasmid DNA or maintained in vivo for a shorter time period. The level of CAT activity was directly related to both the amount of DNA injected and the length of incubation following the injection. The human β-actin promoter was chosen because it has been shown to be a high-level expression promoter in a variety of myogenic cell lines [Gunning et at., supra]. These results showed a short-term dose-response such that increased amounts of DNA were more active at shorter incubation periods. At seven days postinjection, CAT activity was reproducibly detected for all amounts of DNA injected.

A dose- and time-response study was conducted with the pRSV-luciferase plasmid to determine the optimal amount of pRSV-luciferase DNA to be used as an internal DNA uptake control in coinjection experiments. Three mice for each datapoint were injected with different doses of pRSV-luciferase and sampled either seven or 35 days later. The mice were injected with 2.5, 5, 10, 20, or 40 µg of the pRSV-luciferase plasmid in 100 µl normal saline. Control mice were injected with 20 µg of pUC18 DNA that did not contain either the promoter or reporter gene. Luciferase activity was detectable for all concentrations of injected pRSV-luciferase DNA at both seven and 35 days of incubation.

The pSV/TnC-F CAT and pRSV-luciferase plasmids were chosen to assess the relationship between CAT and luciferase activities derived from tongues coinjected with equal masses of these plasmids. The expression of the coinjected plasmids provides a means to both monitor DNA uptake and normalize the data of independent trials. For each trial and data point, three mice were injected with both pSV/TnC-F CAT and pRSV-luciferase at either 2.5, 5, 10, 20, or 40 of each plasmid. One week later the animals were killed and the tongue homogenates assayed for luciferase and CAT activities. Increases in luciferase activity paralleled increases in CAT activity; thus, the enzyme activity derived from both plasmids was directly correlated with the amount of DNA injected. This correlation of coinjected plasmid expression and mass of DNA injected provides a means to normalize DNA uptake such that differences in CAT activity between different promoters can be assessed.

The expression of nuclear localized β-galactosidase was used to determine both the onset and persistence of expression derived from injected plasmid DNA. The pMaori3 plasmid was used due to the presence of the SV40 large T antigen nuclear localization signal sequence and the CMV promoter, which has been shown to be a strong promoter in a variety of mammalian tissues. Mice were injected with 20 µg of the pMaori3 plasmid and the tongues recovered one, four and eight weeks after direct DNA injection. Nuclear LacZ expression in adult tongue muscle was prominent one week after injection and was persistent for more than two months. The β-galactosidase activity was distributed in nuclei arranged linearly along the myofibers. The presence of the herpes simplex virus origin of DNA replication in the pMaori3 plasmid did not affect these results since the tongue muscle cells were not undergoing DNA replication and the use of other plasmids without this origin also resulted in persistent levels of reporter gene expression. The B-galactosidase detection method provides a sensitive assay for localizing the cells in the tongue muscle that have taken up the foreign DNA and expressed the gene.

The regulation of expression of CAT, luciferase, and β-galactosidase activities by a variety of ubiquitously expressing promoters demonstrated the usefulness of tongue muscle for direct gene transfer. By establishing that increased CAT activity was paralleled by increased luciferase activity, coinjection of pRSV-luciferase with CAT expression plasmids provided a means to functionally analyze muscle gene promoters. Therefore, the tongue model system was used to analyze the regulatory role of the human TnC-F promoter in directing expression of both CAT and β-galactosidase enzyme activities.

The ability of the human TnCF promoter to direct nuclear LacZ expression in tongue myofibers was assessed by constructing the pM3–TnC3 plasmid for direct muscle injection studies. The tongues of mice were injected with 25 µg of the pM3–TnC3 plasmid, the tongues were recovered either one or five weeks following injection, and the pattern of LacZ expression determined by X-gal staining. The expression of the LacZ gene driven by the TnC-F promoter was evident at one week following injection and persisted at least five weeks. The number of nuclei containing the β-galactosidase was similar to the number obtained after injection of the pMaori3 plasmid. Thus, the human TnC-F promoter/enhancer was sufficient to direct expression of nuclear localized β-galactosidase activity in tongue myofibers. In the mouse tongue model, the enhancer and proximal promoter elements of the human TnC-F gene were muscle gene regulatory elements suitable for functional analysis.

The quantitative assessment of relative promoter activities used pRSV-luciferase as an internal control for DNA uptake. In all cases each animal received 10 µg of the pRSV-luciferase and 50 µg of the experimental CAT expression plasmid. Based on the previous studies, this quantity of each type of plasmid resulted in CAT and luciferase activities in the linear range, and therefore the luciferase activity in any individual animal would be proportional to the amount of DNA taken up by the muscle. Thus the luciferase activity would control for CAT plasmid uptake and normalize CAT enzyme activity.

The expression of CAT activity by two different promoter-CAT expression plasmids was compared in coinjection experiments. The pSV40 CAT plasmid, which lacked the SV40 enhancer, was chosen as a basal-level expression plasmid [Gorman, C. M. et al. (1982) Mol. Cell. Biol. 2:1044–1051]. Therefore, the pSV40-CAT was used to represent an altered promoter construct with decreased activity analogous to a mutated and inactivated muscle gene promoter. The pTnC-F CAT plasmid was chosen to examine the effects of a muscle-specific promoter element. Mice were coinjected with 10 µg of pRSV-luciferase and 50 µg of either pSV40 CAT or pTnC-F CAT. The tongues were recovered one and four weeks after injection, and each datapoint for each trial used four animals. The level of CAT activity was significantly higher in tongue muscle injected with the pTnC-F CAT plasmid (FIG. 2). At both one and four weeks after injection, the muscle-specific promoter directed a much higher level of CAT expression. The magnitude of CAT activity decreased between one and four weeks; however, the TnC-F promoter was significantly more active (approximately sevenfold higher) at both time points than the SV40 promoter. Thus, differences between basal-level promoter activity and high-level promoter activity can be examined in the mouse tongue model and effectively compared by normalizing DNA uptake with coinjected luciferase activity.

EXAMPLE 2

The production of a potentially active molecule was examined following the injection of a polynucleotide sequence into the tongue muscle. These studies used a plasmid DNA construct with a strong muscle-specific promoter driving the expression of the human growth hormone gene. Growth hormone polypeptide production served both as the reporter molecule for the expression of the injected naked polynucleotide sequence and as evidence that a biologically active molecule would be produced in the striated muscle of the tongue after incorporation of the injected polynucleotide. The polynucleotide was introduced into the tongue muscle following the procedures described in Example 1.

Adult mice were injected with 100 μg of naked polynucleotide plasmid either into the tongue or the limb muscle. The injected plasmid consisted of a muscle specific promoter element (TnC promoter and enhancer elements) driving the expression of the full length human growth hormone (hGH) gene [Selden, R. F. et at. (1986) Mol. Cell. Biol. 6:3173–3179] including a poly A addition signal inserted into a pUG8 plasmid backbone.

The tongue and limb muscle tissue were sampled at several timepoints following the direct injection of the DNA and the amount of hGH present in the tissue was determined by radioimmunoassay. The tongue and limb muscles of four mice injected with hGH DNA were analyzed at each time point following injection for expression of hGH.

The hGH radioimmunoassay (RIA) was accomplished using a commercially available kit manufactured by Nicholls Institute. Generally, the procedure uses two hGH antibodies specific for different epitopes on the hGH polypeptide; one antibody is complexed to biotin and the other labeled with I-125. The antibodies are allowed to bind to their specific sites on the hGH molecule and then mixed with avidin-coated beads, which will bind the biotin conjugates. The beads are washed in phosphate-buffered saline (PBS) with Tween20 and then the amount of I-125 bound to the beads determined by gamma counting the sample. The radioimmunoassay is completed on both protein preparations from injected muscle and known mounts of hGH protein used to generate a standard curve. The concentration of hGH in the injected muscle was determined by calculating the ng/ml by comparing the RIA of the experimental samples with the standard curve. The amount of hGH produced in either the tongue or limb muscles was compared at both the identical sampling timepoints and at different points of time following direct injection into the muscle.

Figure 3:
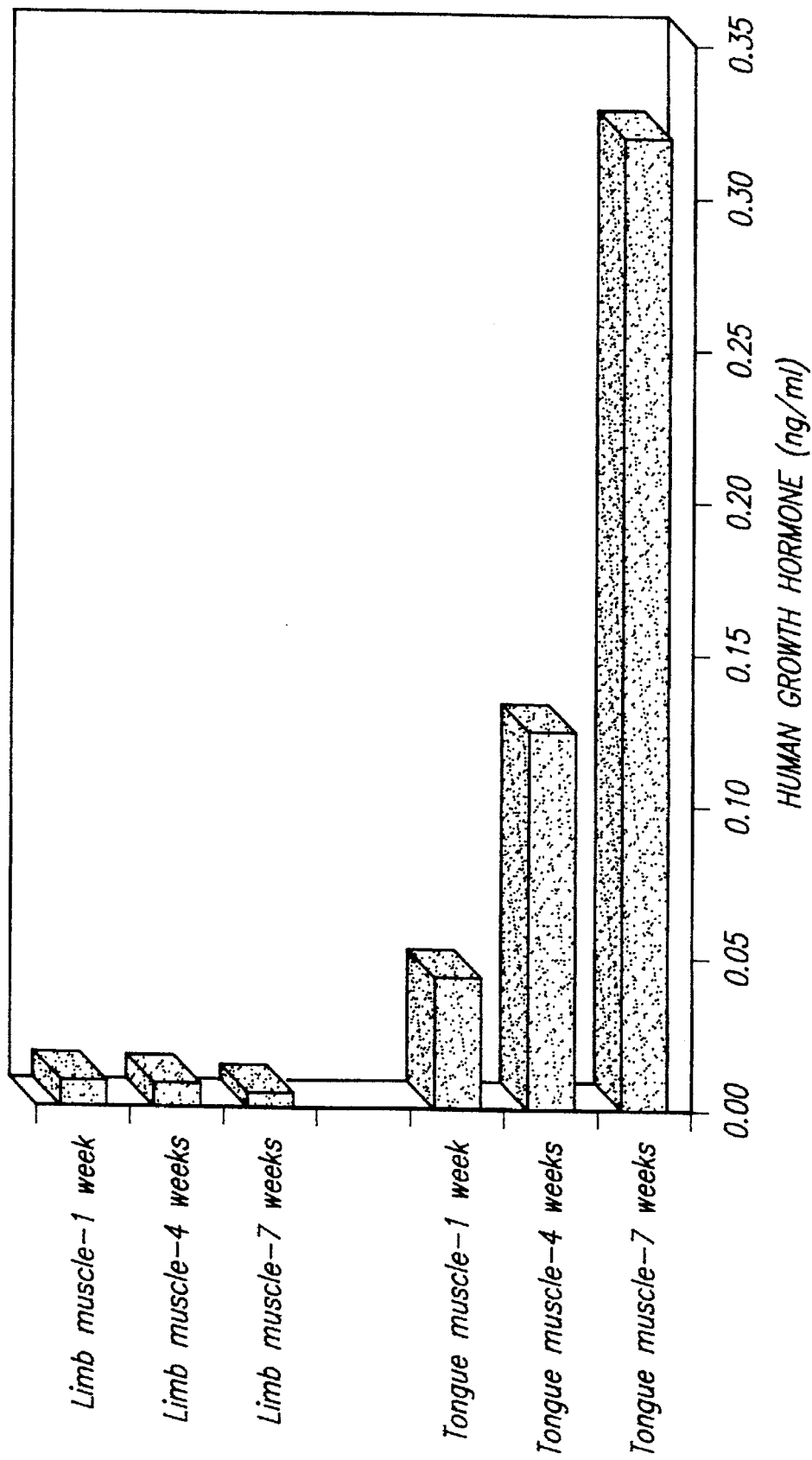
FIG. 3 shows the levels of hGH produced in mice limb and tongue muscles after treatments in accordance with the present invention.

The results of the RIA measurements in CPM are reported in Table 1, and the results of hGH measurements in ng/ml are illustrated in FIG. 3.

TABLE 1

| Animal | Weeks | CPM |
|---|---|---|
| Tongue Muscle Injection | | |
| 1 | 1 | 580 |
| 2 | 1 | 412 |
| 3 | 1 | 834 |
| 4 | 1 | 914 |
| Average: | | 685 |
| 5 | 4 | 809 |
| 6 | 4 | 1048 |
| 7 | 4 | 584 |
| 8 | 4 | 949 |
| Average: | | 847.5 |
| 9 | 7 | 1295 |
| 10 | 7 | 1590 |
| 11 | 7 | 813 |
| 12 | 7 | 857 |
| Average: | | 1138.75 |
| Limb Muscle Injections | | |
| 13 | 1 | 509 |
| 14 | 1 | 374 |
| 15 | 1 | 292 |
| 16 | 1 | 392 |
| Average: | | 391.75 |
| 17 | 4 | 349 |
| 18 | 4 | 361 |
| 19 | 4 | 329 |
| 20 | 4 | 441 |
| Average: | | 370 |
| 21 | 7 | 311 |
| 22 | 7 | 405 |
| 23 | 7 | 364 |
| 24 | 7 | 312 |
| Average: | | 348 |
| Negative Control Tongue Extracts | | |
| | | 283 |
| | | 286 |

The expression of the directly injected hGH DNA was different based on a comparison of the levels of hGH produced in the tongue and limb muscles (Table 1). One week following injection of the plasmid DNA there was no detectable level of expression in the limb muscle when the RIA levels were compared to negative controls. The amount of hGH detected by RIA in the tongue was significantly different than background and could be determined from the standard curve to be approximately 0.05 ng/ml (FIG. 3). At both 4 and 7 weeks following direct injection into the limb muscle, the RIA levels remained at background, and thus no production of hGH protein was detected in the muscle tissue. At 4 and 7 weeks, the tongue muscle contained progressively greater mounts of hGH (0.13 and 0.31 ng/ml, respectively). Thus, the tongue muscle continued to express the exogenous polynucleotide at up to 7 weeks following injection and the levels of expression increased gradually over this period of time. The limb muscle was not observed to express the hGH following percutaneous injection of the hGH plasmid DNA.

EXAMPLE 3

The results of Example 2 provided evidence that a molecule with biological activity could be produced in the striated muscle of the tongue following direct injection of a naked polynucleotide which had a sequence encoding the molecule and a promoter to drive transcription. Furthermore, the results of Example 2 provided evidence that there was enhanced expression of the polynucleotide in the striated muscle of the tongue relative to the amount produced in the striated muscle of the limb. The RIA analysis of the levels of hGH in the tongue muscle documented the production of polypeptide; however, these studies measured only the amount and presence of hGH and not the effect of this molecule following entry into the systemic circulation. The systemic effects and biological activity of the hGH synthesized following incorporation of directly injected hGH specific polynucleotide were examined in a newborn mouse model system.

In mammals, the effects of elevated levels of growth hormone are directed associated with altered morphology [Jadresiz, A. et al. (1982) *Q. J. Med.* 51:189–204]. In humans, elevated levels of pituitary gland produced growth hormone can present with two different phenotypes, which are related to the age of onset of elevated hormone levels. If there are elevated levels of hGH during childhood, the individual may be referred to as a "pituitary giant" and reach heights and weights much in excess of those observed in the general population. If the hGH levels become elevated in a mature adult (due, for example, to a pituitary tumor), then the condition is called "acromegaly" and results in enlargement of the extremities of the skeleton and coarsening of the facial features [Jadresiz et al., supra]. Thus, elevated levels of growth hormone in newborn mice were analyzed to determine whether they were associated with alterations in the rate of growth of the animals. Growth hormone homology is high between species and growth hormone receptors will bind to and respond to growth hormone specific to another species.

Newborn mice were injected with approximately 10 μg of the hGH expression plasmid described in Example 2. The polynucleotide was injected into the tongue of the newborn mice in approximately 15 μl of normal saline. The mice were anesthetized by cold exposure and the tongues were pulled out with a forceps so that the DNA could be injected into the bulk of the tongue muscle. Control mice were similarly injected with normal saline that did not include any polynucleotide and marked by dipping the tip of the tail so that they could be identified at subsequent developmental timepoints. Both the DNA injected and control mice were returned to the dam and reared identically. At specific times following the injection of the hGH DNA, the litter was weighed and the weights of the DNA injected and control mice recorded (Table 2). At the latest time point the mice were sacrificed and their peripheral blood sampled and tongue muscles excised for hGH determinations by RIA.

Figure 4:
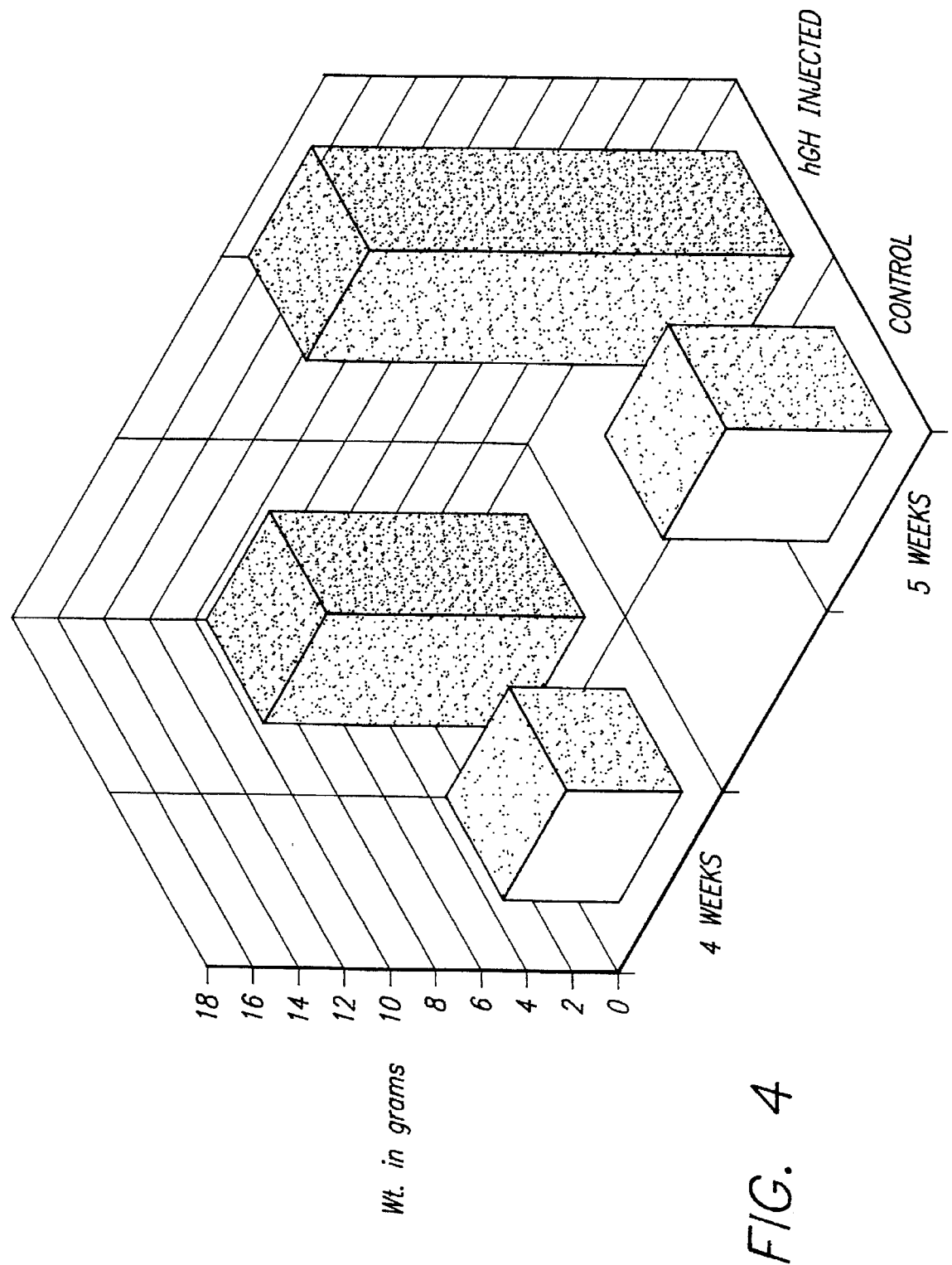
FIG. 4 illustrates the increases in weight in experimental animals following delivery of a polynucleotide encoding hGH in accordance with the present invention compared to untreated control animals.

The results of the weight determinations are reported in Table 2 and depicted in FIG. 4.

TABLE 2

| Animal # | Weight (g) Four weeks | Weight (g) Five weeks |
| --- | --- | --- |
| hGH Injected Animals | | |
| 1 | 11.75 | 18.56[a] |
| 2 | 10.2 | 16.92[a] |
| 3 | 11.54 | 18.3[a] |
| 4 | 10.96 | 17.8[a] |
| 5 | 11.76[a] | — |
| Average: | 11.242 | 17.895 |
| Control Animals | | |
| 1 | 6.1 | 7.97[a] |
| 2 | 5.07 | —[b] |
| 3 | 5.6 | —[b] |
| 4 | 4.9 | 6.34[a] |
| Average: | 5.4175 | 7.155 |

[a]Animal sacrificed for hGH determinations
[b]Animal died prior to next scheduled weight measurement The mice that were injected with hGH DNA had a significantly higher weight at both 4 and 5 weeks after injection than their control injected littermates (Table 2, FIG. 4). At 4 weeks after injection the hGH DNA injected mice were nearly twice as heavy as their control littermates, and at 5 weeks following injection the hGH DNA injected mice were 2.5 to 3 times larger than the controls. The hGH DNA injected mice were larger in all proportions than their littermates and were similar in appearance to mice that were several weeks older. The hGH DNA injected mice also developed an altered coat texture and began to dominate their control littermates at the later stages of the study. At 5 weeks following the injections the control mice were only about 75% of the size of the injected mice at 4 weeks following the injection (FIG. 4).

The RIA analysis of the peripheral blood and tongue muscle did not detect any differences in the levels of hGH between the DNA injected and control mice as both groups had RIA data that was at the background level. The dilution of newly-produced hGH in the enlarging muscle of the tongue and the volume of the peripheral blood circulation was below the detectable limit, yet sufficient for a biological effect. Thus, the level of sensitivity of the RIA was not sufficient to detect the hGH produced in the tongue muscle yet there was distinct evidence that the hGH produced had a readily appreciated biological effect following entry into the systemic circulation.

The injection of a naked polynucleotide, which encodes a biologically active peptide, into the tongue muscle was directly associated with a related biological effect— increased size and weight—of the injected mice. Thus, the tongue muscle was capable of expressing a gene for a biologically active peptide and releasing this peptide into the systemic circulation at levels sufficient to cause a systemic effect. This effect was observed over a distinct developmental window during which the neonatal mice are particularly susceptible to the effects of an increased systemic level of growth hormone. Therefore, the tongue muscle is capable of both synthesizing a biologically active molecule from an injected polynucleotide template and releasing this molecule for systemic effect.

EXAMPLE 4

The time course of response of an animal to a biologically active molecule produced in tongue muscle following the direct injection of a polynucleotide encoding that molecule was characterized in adult mice. Adult mice were used so that a biological effect could be analyzed in an animal that was mature and not undergoing developmentally related alterations in the levels of bioactive molecules. The effects of increased levels of erythropoietin (EPO) resulting from the injection of an EPO DNA construct into either tongue muscle or limb muscle was investigated.

Increased levels of EPO result in increased production of red blood cells [Besa, E. C. (1983) "Disorders of red blood cell production and iron metabolism," in *Internal Medicine*, L. F. Rose & D. Kaye eds., C. V. Mosby]. This is manifested as an increase in the hematocrit of the peripheral circulation. In addition, the hematocrit is closely controlled by the organism; sustained elevations in the hematocrit require sustained elevations of EPO. Thus, a biomarker of elevated EPO is increases in hematocrit, and these increases can be closely correlated with the amount of EPO produced from the injected DNA at a defined timepoint following the injection.

Adult mice were injected in either the tongue or hindlimb muscle with an EPO-specific DNA expression construct. The EPO construct consisted of the CMV intermediate early 1 promoter [Boshart et al., supra] driving the human erythropoietin gene sequence [Jacobs, K. et al. (1985) *Nature* 313:806–810; Lin, F. K. et al. (1985) *Proc. Natl. Acad. Sci. USA* 82:7580–7584], which included the entire protein coding region and the poly A addition signal, inserted into a pUC 19 plasmid backbone. Each of the mice received 50 µg of EPO expression plasmid DNA injected into the specific muscle by a percutaneous approach. Thirteen mice received EPO DNA injected into the tongue and twelve animals received EPO DNA injected into the right hind limb muscle. Six additional animals were injected in the tongue with normal saline containing only the pUC 19 plasmid backbone DNA, 50 µg/injection. The animals injected in either the tongue or hind limb muscles were sampled at 4, 7, 14 and 28 days after injection with 3 different animals evaluated at each time in each group. The animals were anesthetized and peripheral blood collected by a percutaneous cardiac puncture approach. The peripheral blood was collected and an aliquot placed into a hematocrit capillary pipette and centrifuged. The hematocrit was measured and calculated as a percentage of the total blood volume centrifuged for each of the control and experimental animals at each time of analysis. The hematocrits obtained were compared based on the method of EPO DNA administration and the time after injection and compared to the hematocrit of the control animals. The results are reported in Table 3 and illustrated in FIG. 5.

TABLE 3

| | Day | Blood Volume | RBC | Hematocrit |
|---|---|---|---|---|
| Control Animals | | | | |
| 1 | 4 | — | — | N.D. |
| 2 | 4 | 1.4 | 0.8 | 0.571429 |
| 3 | 4 | — | — | N.D. |
| 1 | 7 | 0.9 | 0.4 | 0.444444 |
| 2 | 7 | 0.85 | 0.41 | 0.482353 |
| 3 | 7 | 0.5 | 0.5 | 0.454545 |
| | | | Average: | 0.57 |
| | | | Overall control average: | 0.485 |
| Tongue injected | | | | |
| 1 | 4 | 0.95 | 0.5 | 0.526316 |
| 2 | 4 | 1 | 0.51 | 0.51 |
| 3 | 4 | 1.6 | 0.9 | 0.5625 |
| | | | Average: | 0.53 |
| 1 | 7 | 1.2 | 0.8 | 0.666667 |
| 2 | 7 | 1.3 | 0.8 | 0.615385 |
| 3 | 7 | 1.7 | 0.7 | 0.411765 |
| | | | Average: | 0.57 |
| 1 | 14 | 1.5 | 0.8 | 0.533333 |
| 2 | 14 | 1.7 | 0.8 | 0.470588 |
| 3 | 14 | — | — | N.D. |
| | | | Average: | 0.57 |
| 1 | 28 | 1.5 | 0.8 | 0.533333 |
| 2 | 28 | 1.2 | 0.7 | 0.583333 |
| 3 | 28 | 0.7 | 0.3 | 0.428571 |
| 4 | 28 | 1.5 | 0.9 | 0.6 |
| 5 | 28 | — | — | Lost |
| Limb Injected | | | | |
| 1 | 4 | 1 | 0.52 | 0.52 |
| 2 | 4 | — | — | N.D. |
| 3 | 4 | 1.02 | 0.55 | 0.539216 |
| | | | Average: | 0.53 |
| 1 | 7 | 0.9 | 0.5 | 0.555556 |
| 2 | 7 | 1.2 | 0.55 | 0.458333 |
| 3 | 7 | 1.55 | 0.7 | 0.451613 |
| | | | Average: | 0.497 |
| 1 | 14 | 0.5 | 0.24 | 0.48 |
| 2 | 14 | 1.6 | 0.7 | 0.4375 |
| 3 | 14 | — | — | Lost |

TABLE 3-continued

| | Day | Blood Volume | RBC | Hematocrit |
|---|---|---|---|---|
| | | | Average: | 0.46 |
| 1 | 28 | — | — | Lost |
| 2 | 28 | — | — | Lost |
| 3 | 28 | 1.2 | 0.55 | 0.458333 |
| | | | Average: | 0.46 |

The results are summarized in Table 4.

TABLE 4

| | 4 Days | 7 Days | 14 Days | 28 Days |
|---|---|---|---|---|
| Control | 0.485 | | | |
| EPO-Tongue | 0.53 | 0.57 | 0.51 | 0.54 |
| EPO-Limb | 0.53 | 0.497 | 0.46 | 0.46 |

Figure 5:
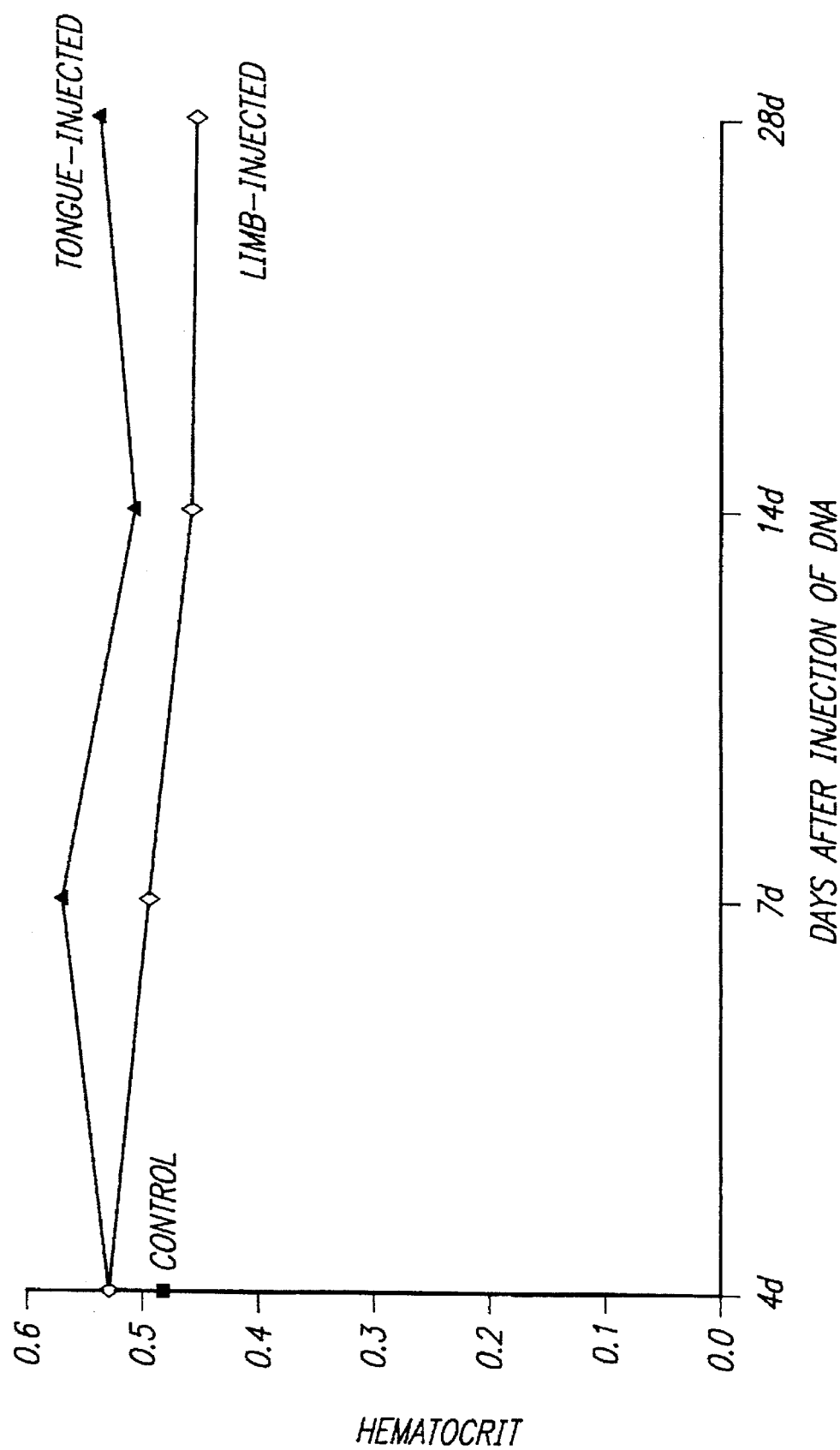
FIG. 5 compares erythropoietin levels in animals injected with a polynucleotide encoding erythropoietin in the tongue with those in animals injected in the limb and with untreated control animals.

EPO DNA injected into both the tongue muscle and hind limb muscle resulted in an increase in the hematocrit at 4 days after injection when compared to the control hematocrit (Tables 3 and 4; FIG. 5). The hematocrit observed in both tongue and hindlimb muscle were similar at 4 days following injection. One week after DNA injection there was a difference in hematocrits associated with the method of DNA injection. The tongue injected animals had a sustained elevation in the hematocrit at a level similar to that observed at 4 days after injection; however, those animals that received injection of the EPO DNA into the hindlimb muscles had hematocrits at the level of the controls. There was a significant difference between the hematocrits in the tongue injected and hindlimb injected animals at the 7 day post-injection timepoint. At all subsequent times following injection (14 and 28 days), the hematocrit remained elevated in the tongue injected mice when compared to both the control and limb injected hematocrits. Thus, the tongue injected mice had a sustained elevation in the hematocrit that was not observed in those mice injected with EPO DNA into the hind limb muscle.

The EPO-associated elevation of the hematocrit is a biological effect which can be easily monitored. This biological response occurs rapidly following the increase in the levels of the biological effector molecule and the response is only sustained when the levels of EPO remain elevated. These results show that injection of an exogenous polynucleotide encoding the erythropoietin molecule into the tongue muscle is associated with a significant and sustained increase in the hematocrit. Furthermore, this sustained increase was not observed when the identical DNA construct was injected into the hindlimb muscle. The tongue muscle was capable of a prolonged elevation in the levels of EPO, resulting in an increase in the direct biological effect (elevated hematocrit).

While the present invention has been described with reference to preferred embodiments and illustrative examples, it should be understood that one of ordinary skill in the art after reading the foregoing specification would be able to effect various changes, substitutions of equivalents and modifications to the compositions and methods as described herein. Therefore, it is intended that the scope of the invention not be limited by reference to the illustrative examples, but rather with reference to the accompanying claims.

What is claimed is:

1. A method of producing a polypeptide in a mammal, comprising:

preparing an expression vector comprising a DNA sequence encoding a polypeptide operatively linked to a promoter; and injecting said expression vector into the tongue muscle of said mammal, whereby said polypeptide is expressed at a detectable level.

2. A method according to claim 1, wherein the expression vector comprises a plasmid.

3. A method according to claim 2, wherein the plasmid further comprises a replicator.

4. A method according to claim 2, wherein the plasmid further comprises at least one enhancer region.

5. A method according to claim 1, wherein the promoter is muscle-specific.

6. A method according to claim 1, wherein the expression vector is administered at a dose in the range of about 0.01 µg/kg to about 100 mg/kg of body weight.

7. A method according to claim 6, wherein the dose is in the range of about 0.001 mg/kg to about 10 mg/kg.

8. The method of claim 1, wherein the polypeptide is a biologically active polypeptide.

9. The method of claim 8, wherein the biologically active polypeptide is a growth factor or growth hormone.

* * * * *

UNITED STATES PATENT AND TRADEMARK OFFICE
CERTIFICATE OF CORRECTION

PATENT NO. : 5,656,610

DATED : August 12, 1997

INVENTOR(S) : Shuler et al.

It is certified that error appears in the above-indentified patent and that said Letters Patent is hereby corrected as shown below:

| Column | Line | |
|---|---|---|
| 1 | 26 | Change "acid" to --Acsadi-- |
| 5 | 66 | Change "pg" to --p$\beta$-- |
| 6 | 51 | Change CoA 5 to --CoA, 5-- |
| 6 | 54 | Change "Speed-Vat" to --Speed-Vac-- |
| 7 | 51 | Change "40" to --40$\mu$g-- |
| 9 | 37 | Change "pUG8" to --pUC8-- |
| 9 | 54 | Change "Tween 20" to --Tween-20-- |
| 13 | 9 | Change "fight" to --right-- |
| 14 | 54 | Change "IPO" to --EPO-- |

Signed and Sealed this

Second Day of December, 1997

*Attest:*

BRUCE LEHMAN

*Attesting Officer*   *Commissioner of Patents and Trademarks*